United States Patent [19]

Grimova et al.

[11] 4,221,919

[45] Sep. 9, 1980

[54] ANTIINFLAMMATORY SUBSTITUTED PHENYLACETIC ACIDS

[75] Inventors: Jaroslava Grimova; Oldrich Nemecek; Miroslav Kuchař; Bohumila Brunová, all of Prague, Czechoslovakia

[73] Assignee: SPOFA, United Pharmaceutical Works, Prague, Czechoslovakia

[21] Appl. No.: 33,147

[22] Filed: Apr. 24, 1979

Related U.S. Application Data

[63] Continuation-in-part of Ser. No. 641,643, Dec. 17, 1975.

[30] Foreign Application Priority Data

Dec. 17, 1974 [CS] Czechoslovakia .................. 8681/74

[51] Int. Cl.$^2$ .............................................. C07C 69/76

[52] U.S. Cl. .................................. 562/465; 424/308; 560/55; 560/74; 544/358

[58] Field of Search ...................... 560/55, 74; 562/465

[56] References Cited

U.S. PATENT DOCUMENTS

3,959,364  5/1976  Armitage et al. ................ 260/575 R

OTHER PUBLICATIONS

Kametani et al., C.A., vol. 64, p. 19702(g) 1966.
Hellmann et al., C.A. 55, p. 19478-9, 1961.

*Primary Examiner*—Paul J. Killos

[57] ABSTRACT

Antiinflammatory substituted phenylacetic acids of low toxicity are prepared by reaction of a salt of an alkyl 3 chloro-4-hydroxyphenylacetate with a substituted benzyl halide in the presence of an inert organic solvent at elevated temperatures.

2 Claims, No Drawings

ANTIINFLAMMATORY SUBSTITUTED PHENYLACETIC ACIDS

This application is a continuation-in-part application of Ser. No. 641,643, filed Dec. 17, 1975, entitled Antiinflammatory Substituted Phenylacetic Acids.

This invention relates to antiinflammatory agents. More particularly, the present invention relates to antiinflammatory substituted phenylacetic acids of low toxicity which are of interest for use in the preparation of medicaments for oral or parenteral applications.

The novel antiinflammatory agents herein described are phenylacetic acid derivatives of the general formula

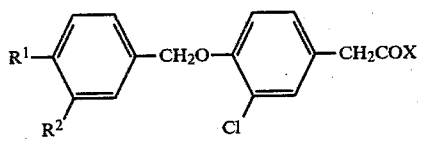

(1)

wherein $R^1$ is selected from the group consisting of hydrogen, saturated and unsaturated carbon chains having from 1–6 carbon atoms, alkoxy and alkenyloxy groups having from 1–6 carbon atoms, $R^2$ is selected from the group consisting of hydrogen and halogen atoms, and an alkyl group having from 1–4 carbon atoms, X is selected from the group consisting of hydroxyl, alkoxy groups having from 1–4 carbon atoms, and $-O(CH_2)_nN(R')_2$, n being an integer from 2–4, $R'$ being an alkyl group having from 1–4 carbon atoms, and salts thereof with pharmaceutically acceptable bases.

Studies have revealed that compounds of the foregoing type evidence outstanding antiinflammatory characteristics, a particular preference being found for 3-chloro-4-benzyloxyphenylacetic acid and 3-chloro-4-(4′-isopropoxy benzyloxy) phenylacetic acid in the form of a salt with cyclohexylamine and N-methylpiperazine.

In accordance with the present invention, the compounds of the invention may conveniently be prepared by reacting a salt of an alkyl 3-chloro-4-hydroxyphenylacetate of the general formula

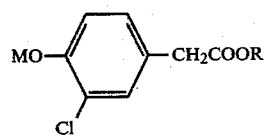

(2)

wherein R is an alkyl group having from 1–4 carbon atoms and M is an alkali metal, with a substituted benzyl halide of the general formula

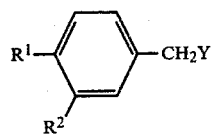

(3)

wherein $R^1$ and $R^2$ are as described in formula (1) and Y is selected from the group consisting of chlorine, bromine and iodine. Reaction of the described compounds is typically effected in an inert organic solvent at a temperature within the range of 60°–100° C. to yield an ester as set forth in the following equation:

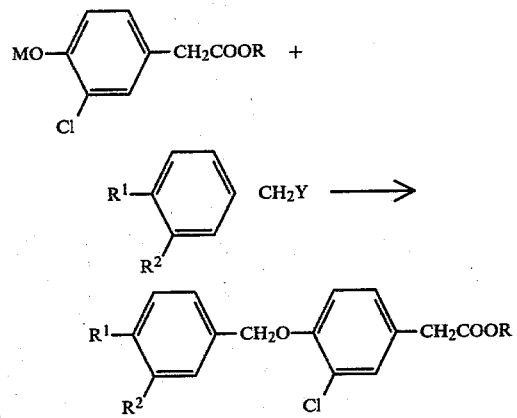

(4)

Inert organic solvents found particularly suitable for this purpose are methanol or dimethylsulfoxide. The ester so obtained may then be saponified to the free acid of formula (1) (wherein X is OH) which may, subsequently, be neutralized with an inorganic or organic base to yield the corresponding salt. This end is conveniently attained by neutralizing the free acid with sodium or potassium hydroxide, cyclohexylamine, N-methylpiperazine and the like. Alternatively, the free acid may be transformed into a halide, as for example, the chloride or bromide, which is reacted with ammonia or butylamine to yield the corresponding amide, or with an amino alcohol of the general formula $$OH(CH_2)_2-N(R')_2 \quad (5)$$

wherein $R'$ is as indicated above.

The above-described saponification process wherein the compound

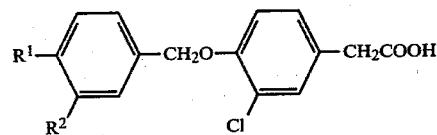

is obtained is most conveniently effected by boiling the ester (4) in an aqueous solution of an alkali metal hydroxide, typically sodium hydroxide. Other procedures for attaining this end may also be employed. Thus, for example, an aldehyde of the general formula

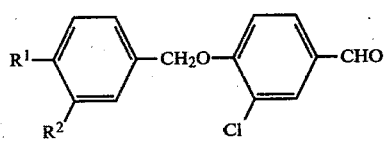

(6)

wherein $R^1$ and $R^2$ are as previously indicated and are reacted with N-benzoylaminoacetic acid to yield the corresponding azlactone which is hydrolyzed to the corresponding α-keto acid. Then, the keto acid is subjected to oxidative decarbonylation to yield the acid of formula (1) (wherein X is hydroxyl). Still another procedure for attaining this end involves oxidizing an aldehyde of the type shown by compound (6) to the corresponding benzoic acid which is converted to the acid of compound (1) (X=OH) by the Arndt-Eistert reaction via the corresponding diazo ketone. Finally, the compound of formula (1), X=OH, may also be produced by reacting an acetophenone of the following formula

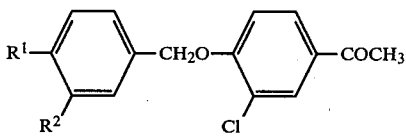

wherein $R^1$ and $R^2$ are as above-designated with sulfur and morpholine to yield the corresponding thiomorpholide of the substituted phenylacetic acid which may then be hydrolyzed to yield the desired product.

As indicated previously, the most advantageous procedure for preparing compounds of formula (1) involves reaction of hydroxyphenylacetates of compound (2) with benzyl halides of the general formula (3). In a typical procedure, the desired ester of formula (2) (wherein M is hydrogen) is obtained by the following sequence of steps:

(a) O-chloroanisole is chloromethylated by reaction with paraformaldehyde and gaseous hydrogen chloride in acetic acid in the presence of a catalyst, such as zinc chloride, to yield 3-chloro-4-methoxybenzyl chloride, (b) the resultant chloride is reacted with an alkali metal cyanide in a solvent, such as dimethyl sulfoxide, at elevated temperatures to yield 3-chloro-4-methoxyphenylacetonitrile, (c) the nitrile is hydrolyzed by boiling with 48% hydrobromic acid to yield 3-chloro-4-hydroxyphenylacetic acid, and (d) the resultant acid is esterified by boiling in an alcohol in the presence of an acid catalyst, such as, p-toluenesulfonic acid, to yield the ester of formula (2) wherein M is a hydrogen atom.

Substituted benzyl chlorides of formula (3) wherein Y is chlorine may readily be obtained from the corresponding substituted benzene derivatives of chloromethylation with a mixture of paraformaldehyde and hydrogen chloride in an inert solvent, the reaction conditions being dependent on the nature of the substituents $R^1$ and $R^2$.

Several examples of the present invention are set forth below. These examples are merely for purposes of exposition and it will be appreciated by those skilled in the art that they do not limit the scope of the invention.

EXAMPLE 1

3-chloro-4-(3'-chloro-4'-methoxybenzyloxy) phenylacetic acid (a) 193 grams of O-chlorophenol was dissolved in a solution comprising 60 grams of sodium hydroxide in 500 milliliters of water. Then, 190 grams of dimethyl sulfate was added to the solution over a period of 1 hour while cooling the solution to a temperature of approximately 10° C. Following, the resultant mixture was heated to a boil over a 3 hour time period. After cooling and the addition of 300 milliliters of water, an oil was formed on the surface of the solution and an aqueous layer extracted with benzene in two 200 milliliter extractions. The benzene extracts were then combined with the separated oil, washed with 1N sodium hydroxide in two 100 milliliter portions, 50 milliliters of 10% sulfuric acid and two 100 milliliter portions of water. Then, the product was dried over magnesium sulfate, the benzene evaporated and distilled in vacuo, so yielding 195 grams (91.5%) of O-chloroanisole boiling at 59°–60° C./1.0 Torr.

(b) A mixture comprising 179 grams of O-chloroanisole, 8.5 grams of arsenic trioxide and 78 grams of paraformaldehyde in 500 ml of acetic acid was saturated with a stream of hydrogen chloride at 45°–50° C. for a period of 6 hours. The mixture was then maintained at 20° C. for 12 hours and poured into 750 ml of water, so resulting in the formation of an oil which was extracted with benzene in three 250 ml extractions. The benzene solution was next washed with a saturated solution of calcium chloride in eight 150 ml portions and dried over magnesium sulfate. Finally, the benzene was evaporated and the resultant 3-chloro-4-methoxybenzyl chloride distilled in vacuum to yield 196 grams (76.4%) having a boiling point within the range of 123°–125° C./3 Torr.

The foregoing procedure yielded 3-chloro-4-alkyloxybenzyl chloride from alkyl 2-chlorophenyl ether, the chloride having a boiling point of 113°–115° C./2.0 Torr., an 89.1% yield of 3-chloro-4-isobutoxybenzyl chloride from isobutyl 2-chlorophenyl ether, b.p. 106°–108° C./0.5 Torr; a 78.3% yield of 3-chloro-4-isopropoxybenzyl chloride from isopropyl 2-chlorophenyl ether, b.p. 96°–98° C./0.25 Torr.

(c) 145 grams of 3-chloro-4-methoxybenzyl chloride was added to a solution comprising 40.6 grams of sodium cyanide in 230 ml of dimethylsulfoxide over a 40 minute time period at a temperature within the range of 40°–45° C. The reaction mixture was then stirred at this temperature for 6 hours and poured into 800 ml of water, the separated oil being extracted with 3 200 ml portions of ether. The ethereal solution was next washed with a dilute (1:1) hydrochloric acid solution in two 100 ml portions, with two 100 ml portions of water and dried over magnesium sulfate. The ether was then driven off, yielding 136.5 grams of crystalline 3-chloro-4-methoxy-phenylacetonitrile, m.p. 54°–56° C., which was refluxed for 16 hours with 420 ml of 48% hydrobromic acid. Following, the reaction mixture was cooled to −5° C. and, after two hours at this temperature, the precipitate filtered, triturated with ether in three 400 ml portions, dried over magnesium sulfate and boiled down to yield 137 grams (97.7%) of 3-chloro-4-hydroxyphenyl acetic acid, m.p. 101°–104° C.

(d) The acid obtained in step (3), 137 grams, was dissolved in 950 ml of methanol and, after the addition of 3.3 grams of p-toluenesulfonic acid the reaction mixture was refluxed for three hours. The major portion of the methanol was then evaporated, the residue diluted with 200 ml. of water and the resultant oil extracted with two 250 ml portions of ether. The ethereal solution was next washed with 150 ml of water and dried over magnesium sulfate. Evaporation of the ether and distillation of the residue in vacuum yielded 94.5 grams (64.2%) of methyl 3-chloro-4-hydroxyphenylacetate, b.p. 141°–143° C./0.4 Torr.

(e) A solution of sodium methoxide was prepared by dissolving 1.45 grams of sodium in 60 ml of methanol. 10 grams of methyl 3-chloro-4-hydroxyphenylacetate followed by 11.5 grams of 3-chloro-4-methoxybenzyl chloride, prepared as in step (b), were gradually added to the solution. The reaction mixture was then refluxed for 16 hours, evaporated in vacuo and the partially crystalline residue treated with 50 ml of water and 100 ml of benzene. The benzene layer was separated, washed with a 5% sodium hydroxide solution (25ml) and with two 100 ml portions of water, drying of the resultant product being effected over magnesium sulfate. The benzene was then evaporated and the residue refluxed for 12 hours with a mixture of 14 grams of potassium hydroxide, 14 ml of water and 80 ml of ethanol. The reaction mixture was evaporated to dryness and the residue treated with 150 ml of water, the turbid solution being filtered with charcoal at 60° C. Hydrochloric acid was added to the filtrate to make it acidic and the product cooled and filtered. Crystallization from methanol yielded 12.5 grams (73.5%) of 3-chloro-4-(3'-chloro-4'-methoxybenzyloxy)phenylacetic acid melting at 150°–151° C.

EXAMPLE 2

The procedure described in Example (1) (e) was repeated wherein 3-chloro-4-alkyloxybenzyl chloride was reacted with methyl 3-chloro-4-hydroxyphenylacetate to yield 3-chloro-4-(3'-chloro-4'-allyloxybenzyloxy) phenylacetic acid (56% yield), m.p. 132°–133.5° C. (ethyl acetate).

EXAMPLE 3

The procedure of Example (1) (e) was repeated wherein 3-chloro-4-isobutyoxybenzyl chloride was reacted with methyl 3-chloro-4-hydroxyphenylacetate to yield 3-chloro-4-(3'-chloro-4'-isobutoxybenzyloxy) phenylacetic acid (52.4yield), m.p. 127.5°–129° C. (methanol-water).

EXAMPLE 4

The procedure described in Example (1) (e) was repeated wherein 3-chloro-4-isopropoxybenzyl chloride was reacted with methyl 3-chloro-4-hydroxybenzyl acetate to yield 3-chloro-4-(3'-chloro-4'-isopropoxybenzyloxy) phenylacetic acid (55.0%); m.p. 129°–130° C. (methanol).

EXAMPLE 5

The procedure described in Example (1) (e) was repeated wherein 3-chloro-4-benzyloxyphenylacetic acid was prepared by reacting benzyl bromide with methyl-3-chloro-4-hydroxyphenyl acetate. The yield was 72.2% and the product had a melting point of 122°–123° C. (methanol-water 3:2).

EXAMPLE 6

3-chloro-4-(4'-methoxybenzyloxy) phenylacetic acid

A solution comprising 108.1 grams of anisole in 450 ml of benzene was cooled to 2° C. and then saturated with gaseous hydrogen chloride for a period of 3 hours at a maximum temperature of 5° C. Then 38.6 grams of paraformaldehyde was added thereto at 20° C. and, following the addition, the reaction mixture was heated to 45° C. and maintained thereat for 1 hour and again cooled to 20° C. Following, gaseous hydrogen chloride was introduced for an additional 5 hours. Next, the aqueous layer was separated and the benzene solution washed with a saturated solution of calcium chloride in eight 150 ml portions and dried over magnesium sulfate. The residue was distilled in vacuum to yield 102.7 grams (65.7%) of 4-methoxybenzyl chloride, b.p. 108°–110° C./12 Torr.

The following procedure yielded: a 44.9% yield of 4-allyloxybenzyl chloride, b.p. 113°–115° C./1.0 Torr from allyl phenyl ether; a 45.3% yield of 4-isobutoxybenzyl chloride, b.p. 102°–104° C./1.0 Torr from isobutyl phenyl ether; a 46.9% yield of 4-isopropylbenzyl chloride, b.p. 76°–7° C./0.6 Torr from isopropyl phenyl ether; a 57.5% yield of 3-methyl-4-methoxybenzyl chloride, b.p. 121°–123° C./12 Torr from O-methylanisole, and a 48% yield of 3-methyl-4-isopropoxybenzyl chloride, b.p. 98°–100° C./0.3 Torr from isopropyl O-tolyl ether.

(f) 10.0 grams of methyl 3-3chloro-4-hydroxyphenylacetate was added to a solution of sodium methoxide, prepared by dissolving 1.7 grams of sodium in 75 ml of methanol. The solution was then evaporated to dryness in vacuum and the residue dissolved in 50 ml of dimethylsulfoxide. Then, a solution comprising 11.9 grams of p-methoxybenzyl chloride in 10 ml of dimethylsulfoxide was added thereto at 20° C. and the reaction mixture heated to a temperature within the range of 90°–100° C. for 6 hours. Following, the mixture was poured into 400 ml of water and the resultant separated oil extracted with two 200 ml portions of ether. The ethereal solution was then washed with a 5% sodium hydroxide solution in two 50 ml rinses and four 100 ml rinses with water, drying being effected over magnesium sulfate. The residue was heated for 7 hours with a mixture comprising 14 grams of sodium hydroxide, 14 ml of water and 80 ml of ethanol. The solution obtained was then evaporated in vacuum and the semi-crystalline residue dissolved in 600 ml of water and filtered with charcoal. The filtrate was next cooled to 0° C. and made acidic by the addition of dilute hydrochloric acid. After cooling, the separated product was filtered and crystallized from aqueous methanol (3:1) to yield 7.1 grams (46.4% yield) of 3-chloro-4-(4'-methoxybenzyloxy) phenylacetic acid, m.p. 150.5°–152° C.

EXAMPLE 7

3-chloro-4-(4'-allyloxybenzyloxy) phenylacetic acid

The noted compound was prepared in accordance with the procedure described in section (f) from 4-allyloxybenzyl chloride and methyl-3-chloro-4-hydroxy-phenylacetate in 49.6% yield, m.p. 106°–107° C. (ethyl acetate).

EXAMPLE 8

3-chloro-4-(4'-isopropoxybenzyloxy) phenylacetic acid was prepared from 4-isopropoxybenzyl chloride and methyl 3-chloro-4-hydroxyphenyl acetate in a 45.8% yield, m.p. 115°–116° C. (methanol-water 2:1).

EXAMPLE 9

3-chloro-4-(4'-isobutoxybenzyloxy) phenylacetic acid was prepared from 4-isobutoxybenzyl chloride and methyl 3-chloro-4-hydroxyphenyl acetate in 49.5% yield, m.p. 106.6°–108° C. (methanol-water 3:1).

EXAMPLE 10

3-chloro-4-(3'-methyl-4'-methoxybenzyloxy) phenylacetic acid was prepared in 63.0% yield by reaction of 3-methyl-4-methoxybenzyl chloride with methyl 3-chloro-4-hydroxyphenyl acetate. The melting point of the product (methanol) was 142°–143° C.

EXAMPLE 11

3-chloro-4-(3'-methyl-4'-isopropoxybenzyloxy) phenylacetic acid was prepared in 35.2% yield, m.p. 104°–105° C. (methanol) by reaction of 3-methyl-4-isopropoxybenzyl chloride with methyl 3-chloro-4-hydroxyphenylacetate.

EXAMPLE 12

3-chloro-4-(4'-ethylbenzyloxy) phenylacetic acid 190 ml of concentrated hydrochloric acid and 97 ml of 85% phosphoric acid were added to a mixture of 106.2 grams of ethylbenzene and 41 grams of paraformaldehyde in 120 ml of acetic acid. The reaction mixture was heated to 100° C. for 5 hours and the oil formed separated with the aqueous layer being extracted twice with 200 ml portions of ether. The ethereal extracts were then combined with the oil and the solution washed five times with 200 ml portions of water and dried over magnesium sulfate. Finally, the ether was evaporated and the residue fractionated in vacuum. The first fraction comprised 48 grams of unreacted ethylbenzene having a boiling point of 35°–40° C. at 16 Torr and the second fraction comprised 4-ethylbenzyl chloride having a boiling point of 102°–104° C. at 16 Torr (33.6% yield).

The foregoing procedure was employed to prepare the following compounds:

4-isopropylbenzyl chloride having a boiling point of 108°–110° C. at 4.0 Torr from isopropylbenzene (23.8% yield and 57% conversion), 4-isobutylbenzyl chloride having a boiling point of 123°–125° C. at 15 Torr from isobutylbenzene (26.2% yield and 59% conversion).

EXAMPLE 13

3-chloro-4-(4'-isopropylbenzyloxy) phenylacetic acid was prepared in accordance with the procedure designated (f) above by reacting 4-isopropylbenzyl chloride with methyl 3-chloro-4-hydroxyphenylacetate. The resultant product evidenced a melting point of 146.5°–148° C. in a methanol-water 2:1 mixture.

EXAMPLE 14

3-chloro-4-(4'-isobutylbenzyloxy) phenylacetic acid was prepared in accordance with the procedure designated (f) above by reacting 4-isobutylbenzyl chloride and methyl 3-chloro-4-hydroxyphenylacetate. The resultant product evidenced a melting point of 97°–99° C. (methanol-water 4:1), the yield being 61%.

EXAMPLE 15

3.0 grams of cyclohexylamine in 10 ml of acetone was added to a solution of 3-chloro-4-benzyloxyphenylacetic acid (5.6 grams) in 75 ml of acetone. The reaction mixture was stirred for 2 hours at 20° C. and cooled to 0° C., so yielding a precipitate which was filtered and washed thoroughly with cold acetone. The resultant product comprised 6.9 grams of cyclohexylammonium 3-chloro-4-benzyloxyphenylacetate having a melting point of 106°–107° C.

EXAMPLE 16

The procedure of Example 15 was repeated with the exception that 3-chloro-4-(4'-isobutoxybenzyloxy) phenylacetic acid was employed, so yielding an 89.6% yield of the corresponding acetate having a melting point of 148°–149° C.

EXAMPLE 17–19

The procedure of Example 15 was repeated to yield (a) cyclohexylammonium 3-chloro-4-(3'-chloro-4'-methoxybenzyloxy) phenyl acetate in 93.8% yield and a m.p. of 138° C., (b) cyclohexylammonium 3-chloro-4-(3'-methyl-4'-allyloxybenzyloxy) phenylacetate in 89.6% yield and a m.p. of 148°–149° C., and (c) cyclohexylammonium 3-chloro-4-(4'-isopropylbenzyloxy) phenylacetate in 87.2% yield and having a m.p. of 145°–146° C.

EXAMPLE 20

A solution comprising 3.0 grams of N-methylpiperazine in 10 ml of acetone was added to a solution comprising 6.8 grams of 3-chloro-4-(3'-chloro-4'-methoxybenzyloxy) phenylacetic acid in 75 ml of acetone, the reaction mixture being stirred for two hours at 20° C. After cooling to 0° C. and standing overnight thereat a precipitate was formed and, subsequently, filtered and washed with cold acetone. The resultant product comprised 8.8 grams of N-methyl-piperazinium 3-chloro-4-(3'-chloro-4'-methoxybenzyloxy) phenylacetate, m.p. 142°–143° C.

EXAMPLE 21

An 82.8% yield of N-methylpiperazinium 3-chloro-4-(4'-allyloxybenzyloxy) phenylacetate having a m.p. of 99°–100° C. was prepared in accordance with the procedure of Example 20.

EXAMPLE 22

A 92% yield of N-methylpiperazinium 3-chloro-4-benzyloxyphenylacetate having a melting point of 117°–117.5° C. was prepared in accordance with the procedure of Example 20.

EXAMPLE 23

6.15 grams of 3-chloro-4-benzyloxyphenylacetic acid was converted into the corresponding chloride by treatment with 15 ml of thionyl chloride in 50 ml of benzene. A solution comprising 1.85 grams of dimethylaminoethanol in 10 ml of benzene was slowly added at 20° C. to the chloride solution. The mixture was then permitted to stand for 2 hours at that temperature and then cooled to 5° C., so yielding a precipitate which was filtered and washed with benzene. Two crystallizations from ethylacetate-isopropyl alcohol (1:1) yielded 5.6 grams (68.4%) of β-dimethylaminoethyl 3-chloro-4-benzyloxyphenylacetate hydrochloride, m.p. 138°–140° C.

EXAMPLE 24

A solution of the acid chloride prepared in Example 23, in 50 ml of benzene, was added at 10° C. to a pre-cooled mixture of isobutyl alcohol (10 ml) and 20 ml of benzene. The mixture was stirred for 30 minutes at 10° C. and 1 hour at 20° C. and then poured into 200 ml of water. The benzene layer was next separated, washed with 50 ml of a 10% sodium hydroxide solution, twice with 100 ml portions of water and dried over magnesium sulfate. Evaporation of the benzene yielded 5.2 grams (78.1%) of crystalline isobutyl 3-chloro-4-benzyloxyphenylacetate, m.p. 31°–32° C.

In order to demonstrate the efficacy and toxicity of the compounds described above, experiments were performed as described below.

As experimental models of inflammation, serving for testing the antiinflammatory activity, there were used the method of kaolin-induced edema of rat hind limb (Hillebrecht J.: Arzneim-Forsch. 9, p. 625, 1959). Kaolin edema of rat hind limb was induced by subplantar injection of 10% kaolin suspension dosed 0.1 ml per animal. The substances tested were administered once, one hour before the injection of kaolin, by gavage with the aid of a metallic gastric sound in the form of aqueous suspension with gum acacia added, in volumes of 1 ml/100 g body weight, equivalent to doses of 25 and 100 mg/kg. The edema of the right hind limb was measured volumetrically on a Volumometer Ugo Basile at hours 1; 1.5; 3; 4.5 and 6 after injection of kaolin. Statistical evaluation was always made in comparison with an untreated control group, and the efficacy of each compound was expressed in percent inhibition of inflammation. Experimental animals: female rats, Wistar strain, Konarovice breed, weighing 130–150 g, experimental groups of 6 animals each. Pelleted diet and drinking water were served ad libitum. This phase of limb edema induced by injection of kaolin suspension represents an acute phase of inflammatory reaction. In addition, orientative tests for oral acute toxicity were carried out with the compounds tested in female mice, S strain, Konarovice breed, weighing 16–20 g. Each compound was administered once by gavage, dosed 1 g/kg, in the form of aqueous suspensions with gum acacia added. Experimental groups of 5 animals each were employed. The deaths were checked for 1 week after administration.

The phenylacetic acids substituted with chlorine in the meta-position and with benzyloxy group in the para-position exhibit high antiinflammatory activity. On the contrary, similarly substituted derivatives of alpha-phenylpropionic acid show minimal antiinflammatory effect evaluated by the kaolin edema inhibition. Several examples of the derivatives of alpha-arylpropionic acid in comparison with those of phenylacetic acid prove the obvious differences in antiinflammatory effect of the above-mentioned compounds as evident from Tables 1 and 2.

TABLE 1
DERIVATIVES OF ALPHA-ARYLPROPIONIC ACID

| Compounds | $LD_{50}$ oral mice | Kaolin edema inhibition (%) dose: 25 mg/kg |
|---|---|---|
| α-(3-Chloro-4-benzyloxyphenyl)-propionic acid | = 1 g/kg | 14$^n$ |
| α-[3-Chloro-4-(3'-chloro-4'-methoxybenzyloxy)phenyl] propionic acid | <1 g/kg | 9$^n$ |
| α-[3-Chloro-4-(4'-chlorobenzyloxy)-phenyl] propionic acid | >1 g/kg | 25$^+$ |
| α-[3-Chloro-4-(4'-isopropoxybenzyloxy)phenyl] propionic acid | <1 g/kg | 0 |

$^+$effect is statistically significant
$^n$effect is not statistically significant

TABLE 3
DERIVATIVES OF ARYLACETIC ACID

| Compounds | $LD_{50}$ oral mice | Kaolin edema inhibition (%) dose: 25 mg/kg |
|---|---|---|
| 3-Chloro-4-benzyloxyphenyl-acetic acid | >1 g/kg | 39$^+$ |
| 3-Chloro-4-(3'-chloro-4'-methoxybenzyloxy) phenylacetic acid | >1 g/kg | 17$^+$ |
| 3-Chloro-4-(4'-chlorobenzyloxy) phenylacetic acid | >1 g/kg | 28$^+$ |
| 3-Chloro-4-(4'-isopropoxybenzyloxy) phenylacetic acid | <1 g/kg | 29$^+$ |

$^+$effect is statistically significant

From the results shown in the above Tables 1 and 2, it is evident that the group of derivatives of phenylacetic acid exhibit a high antiinflammatory efficacy, one which is substantially greater than those of alpha-phenylpropionic acid.

What is claimed is:
1. 3-Chloro-4-(3'-chloro-4'-methoxybenzyloxy) phenylacetic acid.
2. 3-Chloro-4-(3'-chloro-4'-allyloxybenzyloxy) phenylacetic acid.

* * * * *

UNITED STATES PATENT AND TRADEMARK OFFICE
CERTIFICATE OF CORRECTION

PATENT NO. : 4,221,919
DATED : September 9, 1980
INVENTOR(S) : Jaroslava GRIMOVA ET AL It is certified that error appears in the above-identified patent and that said Letters Patent are hereby corrected as shown below:

On the title page of the patent document change the name on line 2 of the first inventor from "Grimova" to --KUCHAR--

Under the title "Inventors:" the names of inventors should be in the following order -- Miroslav KUCHAR, Bohumila BRUNOVA, Jaroslava GRIMOVA, Oldrich NEMECEK--

Signed and Sealed this

Eighteenth Day of November 1980

[SEAL]

Attest:

SIDNEY A. DIAMOND

Attesting Officer        Commissioner of Patents and Trademarks